(12) United States Patent
Sell et al.

(10) Patent No.: US 6,227,032 B1
(45) Date of Patent: May 8, 2001

(54) SURFACE DURABILITY ROLL TESTER

(75) Inventors: David Joe Sell, Ypsilanti; Perry Edward Phelan, Harsens Island, both of MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/222,355

(22) Filed: Dec. 29, 1998

(51) Int. Cl.[7] ............................. G01N 3/56; G01M 13/02
(52) U.S. Cl. ....................................... 73/7; 73/162
(58) Field of Search ............................................ 73/7, 162

(56) References Cited

U.S. PATENT DOCUMENTS

| | | |
|---|---|---|
| 2,561,133 | 7/1951 | Petkewicz ................... 73/7 |
| 3,383,591 | 5/1968 | Roberts . |
| 4,914,958 | 4/1990 | van Damme ............... 73/7 X |
| 5,373,723 | * 12/1994 | Chou ........................... 73/9 |
| 5,665,900 | * 9/1997 | Yoo ............................. 73/7 |
| 6,119,564 | * 9/2000 | Claus .......................... 73/7 |

* cited by examiner

Primary Examiner—Thomas P. Noland
(74) Attorney, Agent, or Firm—Frank G. McKenzie

(57) ABSTRACT

A surface durability roll tester includes a rotatable tapered center roller and a plurality of rotatable tapered pinion rollers engaging the tapered centered roller to simulate gear teeth geometry and kinematics when the tapered center roller and the tapered pinion rollers are rotated. Sliding and Pure rolling motion can be simulated.

20 Claims, 2 Drawing Sheets

SURFACE DURABILITY ROLL TESTER

BACKGROUND OF THE INVENTION

1. Field of the Invention

The present invention relates generally to roll testers and, more particularly, to a surface durability roll tester for simulating gear teeth geometry and kinematics.

2. Description of the Related Art

It is known to provide a roll tester. A roll tester is a machine that is used to evaluate the effects of materials, manufacturing processes and operating conditions on the performance of components that are subjected to rolling, sliding or combinations of rolling and sliding contact with another component. For example, gears and bearings are components that are subjected to rolling and sliding contact with another component. The roll tester typically includes two cylindrical rolls, which are driven independently at two different speeds. The contact pressure between the two rollers is accomplished by applying a load on each end of one of the rollers directed toward the center of the other roller. The speeds and pressure in which the rollers are driven are chosen to simulate a particular operating condition, which is of interest. The speeds of the rollers can be chosen to simulate pure rolling or varying degrees of positive and negative sliding. A test is accomplished by setting the speeds of each roller to obtain the desired sliding and rolling velocity and setting the contact pressure to the desired pressure that simulates the conditions under investigation. These test conditions are held constant throughout the test. The test is concluded when a predetermined amount of damage is produced in the rollers.

Although the above roll tester has worked well, it suffers from the disadvantage that the straight cylindrical rolls on the roll tester do not simulate the geometry and velocity of gear teeth. Another disadvantage of the above roll tester is that the straight cylindrical rolls do not allow contact loads to be applied effectively. Yet another disadvantage of the above roll tester is that the straight cylindrical rolls do not accurately simulate the geometry and velocity of gear teeth. Therefore, there is a need in the art to provide an improved surface durability roll tester.

SUMMARY OF THE INVENTION

Accordingly, the present invention is a surface durability roll tester. The surface durability roll tester includes a rotatable tapered center roller and a plurality of rotatable tapered pinion rollers engaging the tapered center roller to simulate gear teeth geometry and kinematics when the tapered center roller and the tapered pinion rollers are rotated.

One advantage of the present invention is that a surface durability roll tester using tapered rollers is provided for simulating gear teeth geometry and kinematics. Another advantage of the present invention is that the surface durability roll tester uses tapered rollers to simulate the sliding/rolling action of meshing gear teeth. Yet another advantage of the present invention is that the surface durability roll tester allows contact loads to be applied. Still another advantage of the present invention is that the surface durability roll tester simulates the geometry and the velocities of gear teeth better than straight cylindrical rollers.

Other features and advantages of the present invention will be readily appreciated, as the same becomes better understood after reading the subsequent description taken in conjunction with the accompanying drawings.

DESCRIPTION OF THE PREFERRED EMBODIMENT(S)

Figure 1:
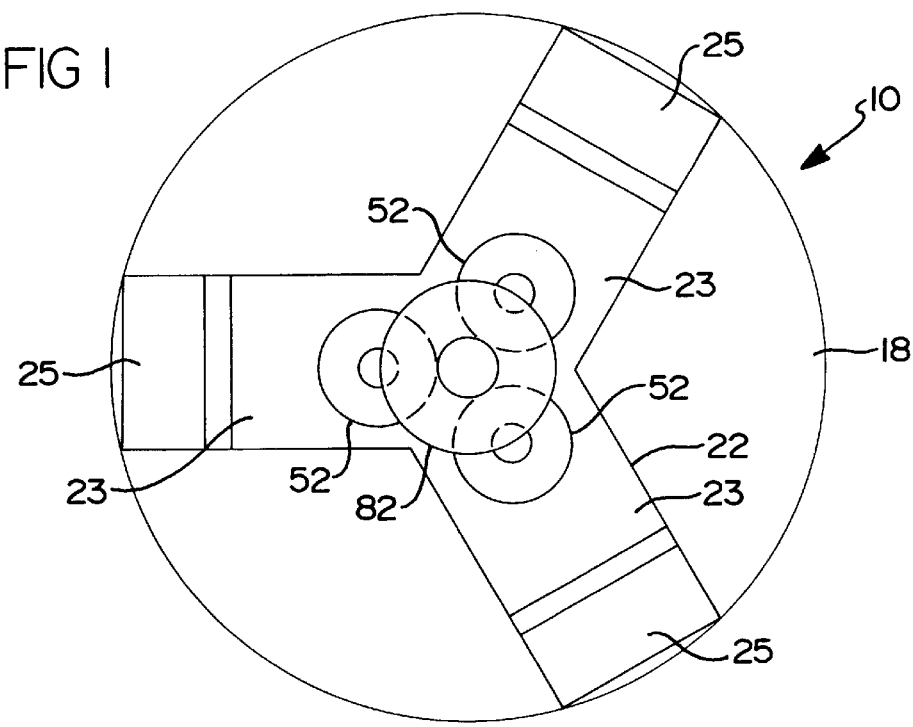
FIG. 1 is an end view of a surface durability roll tester, according to the present invention.
Figure 2:
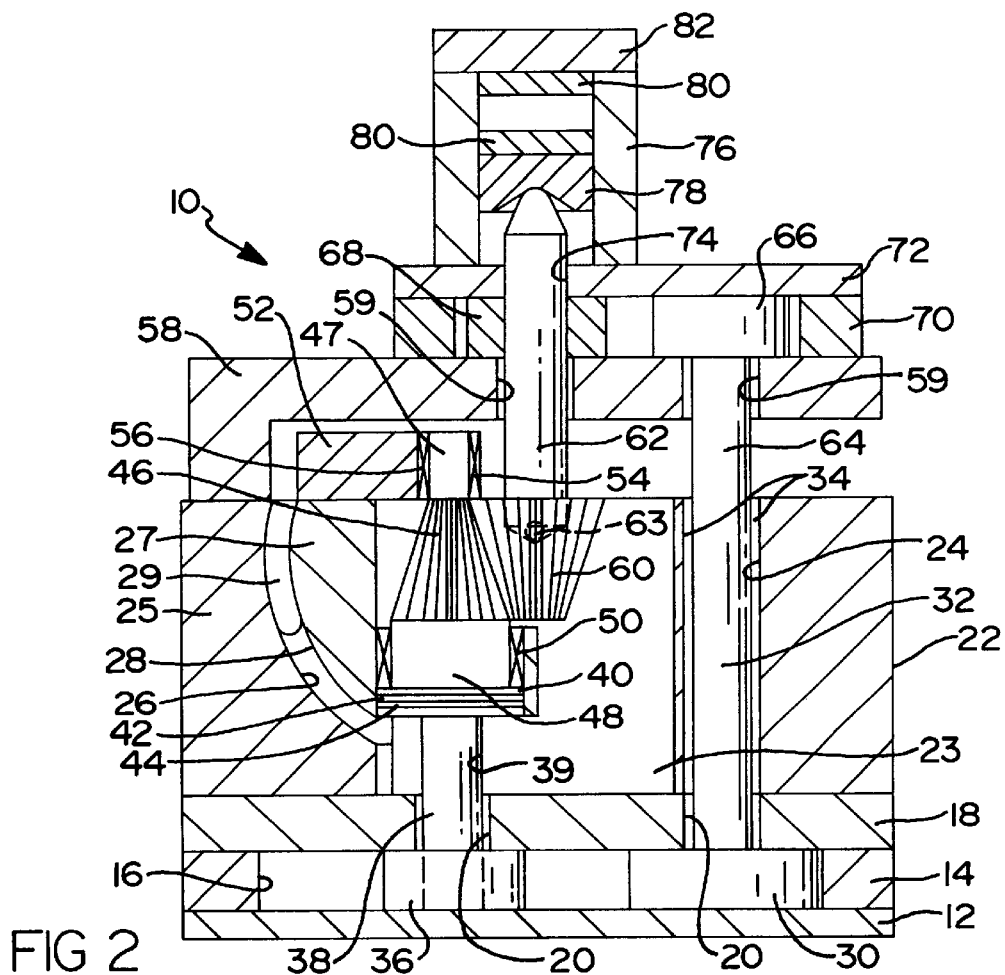
FIG. 2 is a fragmentary top view of the surface durability roll tester of FIG. 1.

Referring to the drawings and in particular FIG. 1 and FIG. 2, one embodiment of a surface durability roll tester 10, according to the present invention, is illustrated. The surface durability roll tester 10 is used to simulate the sliding/rolling action of meshing gear teeth, gear teeth geometry and kinematics. It should be appreciated that surface durability roll tester 10 is used similar to roll testers known in the art.

Figure 3:
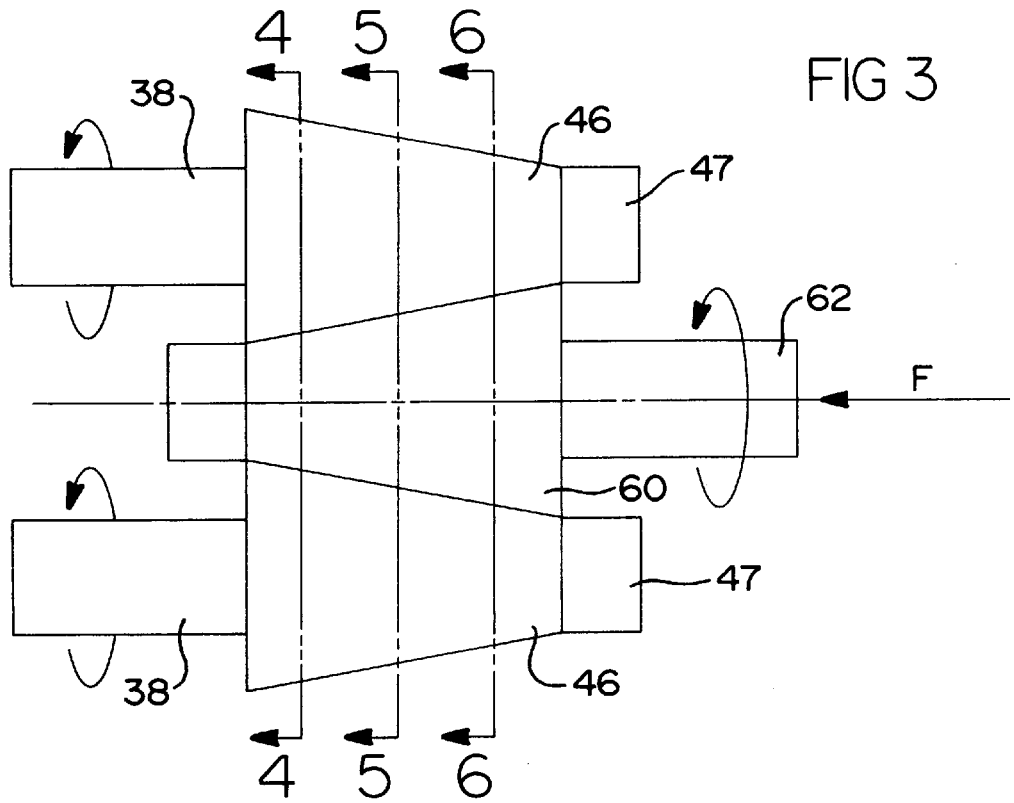
FIG. 3 is a top view of a portion of the surface durability roll tester of FIG. 1.

Referring to FIGS. 1 through 3, the surface durability roll tester 10 includes a bottom gear cover 12. The bottom gear cover 12 is a generally planar plate having a generally circular shape. The bottom gear cover 12 is made of a metal material such as steel. The surface durability roll tester 10 also includes a bottom gear spacer 14 disposed adjacent the bottom gear cover 12. The bottom gear spacer 14 is a generally planar plate having a generally circular shape. The bottom gear spacer 14 has an aperture 16 extending axially therethrough for a function to be described. The bottom gear spacer 14 is made of a metal material such as steel. The surface durability roll tester 10 includes a bottom plate 18 disposed adjacent the bottom gear spacer 14. The bottom plate 18 is generally planar and circular in shape. The bottom plate 18 has a plurality of apertures 20 extending axially therethrough for a function to be described. The bottom plate 18 is made of a metal material such as steel.

The surface durability roll tester 10 further includes a pie spacer 22 disposed adjacent the bottom plate 18. The pie spacer 22 extends axially and has a plurality of, preferably three arms 23 extending radially. The arms 23 are generally rectangular shaped and spaced equally or one hundred twenty degrees from each other. The pie spacer 22 has an aperture 24 extending axially through one of the arms 23 for a function to be described. The pie spacer 22 is made of a metal material such as steel.

The surface durability roll tester 10 also includes a plurality of, preferably three planet reactors 25 disposed adjacent the bottom plate 18 and spaced radially from the arms 23 of the pie spacer 22. Each planet reactor 25 extends axially and radially. Each planet reactor 25 has a width substantially equal to a width of the arm 23 and has a generally arcurate inner surface 26. Each planet reactor 25 is made of a metal material such as steel. The surface durability roll tester 10 includes a plurality of, preferably three planet mounts 27 spaced radially from the planet reactors 25. Each planet mount 27 extends axially and radially. Each planet mount 27 has a width substantially equal to a width of the arm 23 and has a generally arcuate outer surface 28. Each planet mount 27 is made of a metal material such as steel.

The surface durability roll tester 10 includes a plurality of, preferably thirty-six needles 29 disposed between the planet reactors 25 and the planet mounts 27. The needles 29 have a generally circular cross-sectional shape and are generally arcuate in shape to be complementary to the inner surface 26 and outer surface 28. The needles 29 are made of a metal material. It should be appreciated that the needles 29 allow rotational movement between the planet mounts 27 and planet reactors 25.

The surface durability roll tester 10 also includes at least one first gear 30 disposed in the aperture 16 of the bottom gear spacer 14 between the bottom gear cover 12 and the bottom plate 18. The first gear 30 is generally planar and circular in shape. The first gear 30 has a predetermined number of teeth such as thirty-one (31). The first gear 30 is made of a metal material such as steel. The surface durability roll tester 10 further includes an inner driveshaft 32 extending axially through one of the apertures 20 in the bottom plate 18 and the aperture 24 of the pie spacer 22. The driveshaft 32 is generally cylindrical and circular in cross-sectional shape. The driveshaft 32 has one end connected to the first gear 30. The driveshaft 32 is made of a metal material such as steel.

The surface durability roll tester 10 includes a plurality of, preferably six, needles 34 disposed in the aperture 24 between the driveshaft 32 and the pie spacer 22. The needles 34 extend axially and are generally circular in cross sectional shape. The needles 34 are made of a metal material. It should be appreciated that the needles 34 allow rotational movement between the driveshaft 32 and pie spacer 22.

The surface durability roll tester 10 includes at least one, preferably three, second gear 36 disposed in the aperture 16 of the bottom gear spacer 14 between the bottom gear cover 12 and the bottom plate 18. The second gear 36 is generally planar and circular in shape. The second gear 36 has a predetermined number of teeth such as twenty-four (24). The second gear 36 is made of a metal material such as steel. The surface durability roll tester 10 also includes at least one, preferably three, pinion driveshaft 38 extending axially through another one of the apertures 20 in the bottom plate 18 and an aperture 39 in the arm 23 of the pie spacer 22. The pinion driveshaft 38 is generally cylindrical and circular in cross-sectional shape. The pinion driveshaft 38 has one end connected to the second gear 36. The pinion driveshaft 38 is made of a metal material such as steel. It should be appreciated that the first gear 30 and second gear 36 are connected by suitable means such as a belt (not shown) to a source such as a motor (not shown) to rotate the first gear 30 and second gear 36.

The surface durability roll tester 10 further includes at least one thrust bearing 40, thrust washer 42 and snap ring 44 disposed about each pinion driveshaft 38 adjacent the pie spacer 22. The thrust bearing 40, thrust washer 42 and snap ring 44 are generally planar and circular in shape. The thrust bearing 40, thrust washer 42 and snap ring 44 are made of a metal material such as steel.

The surface durability roll tester 10 includes at least one pinion cone 46 connected to one end of each pinion driveshaft 38 adjacent the thrust bearing 40. The pinion cone 46 has a frusta-conical shape with a small diameter shaft end 47 and a large diameter shaft end 48 connected to the pinion driveshaft 38. It should be appreciated that the pinion cone 46 forms a tapered roller.

The surface durability roll tester 10 also includes at least one needle 50 disposed about each pinion cone 46 between the large diameter end 48 and the pie spacer 22. It should be appreciated that the needles 50 allow rotational movement of the pinion cone 46 relative to the pie spacer 22 and planet mount 27.

The surface durability roll tester 10 further includes at least one planet cap 52 connected to each pinion cone 46. The planet cap 52 is generally planar and circular in shape. The planet cap 52 has an aperture 54 extending axially therethrough. The small diameter shaft end 47 of the pinion cone 46 is received in the aperture 54. The planet cap 52 is made of a metal material such as steel. The surface durability roll tester 10 includes at least one needle 56 disposed in the aperture 54 about the small diameter shaft end 47 of each pinion cone 46. It should be appreciated that the needle 56 allows rotational movement between the pinion cone 46 and the planet cap 52.

The surface durability roll tester 10 also includes a top cover 58 disposed adjacent the planet reactors 25 and secured by suitable means such as screws (not shown) extending through the bottom gear cover 12, bottom plate 18, planet reactors 25 and top cover 58. The top cover 58 has a generally inverted "L" shape and a plurality of apertures 59 extending axially therethrough for a function to be described. The top cover 58 is made of a metal material such as steel.

The surface durability roll tester 10 further includes a sun cone 60 disposed adjacent and engaging the pinion cones 46. The sun cone 46 has a generally frusta-conical shape. The sun cone 60 is made of metal material such as steel. It should be appreciated that the sun cone 60 forms a tapered roller.

The surface durability roll tester 10 includes a sun driveshaft 62 attached to the sun cone 60 at its larger diameter end. The sun driveshaft 62 is generally cylindrical and circular in cross-sectional shape. The sun driveshaft 62 extends axially through one of the apertures 59 in the top cover 58. The sun driveshaft 62 is made of a metal material such as steel. The surface durability roll tester 10 also includes a thrust ball 63 disposed between the sun driveshaft 62 and the sun cone 60. The thrust ball 63 is made of a metal material such as steel. It should be appreciated that the thrust ball 63 allows thrust loads to be transferred between the sun driveshaft 62 and the sun cone 60.

The surface durability roll tester 10 further includes a transfer shaft 64 connected to the inner driveshaft 32. The transfer shaft 64 is generally cylindrical and circular in cross-sectional shape. The transfer shaft 64 extends axially through the other one of the apertures 59 in the top cover 58. The transfer shaft 64 is made of a metal material such as steel. It should be appreciated that the transfer shaft 64 may be integral with the inner driveshaft 32.

The surface durability roll tester 10 includes at least one third gear 66 connected to the end of the transfer shaft 64. The third gear 66 is generally planar and circular in shape. The third gear 66 has a predetermined number of teeth such as twenty-four (24). The third gear 66 is made of a metal material such as steel. The surface durability roll tester 10 also includes a fourth gear 68 attached to one end of the sun drive shaft 62. The fourth gear 68 is generally planar and circular in shape. The fourth gear 68 has a predetermined number of teeth such as twenty-four (24). The fourth gear 68 is made of a metal material such as steel. It should be appreciated that the third gear 66 and fourth gear 68 are interconnected by suitable means such as a belt (not shown) to allow the third gear 66 to rotate the fourth gear 68.

The surface durability roll tester 10 further includes a gear spacer 70 disposed adjacent the top cover 58. The gear spacer 70 is a ring member having a generally circular shape. The gear spacer 70 is disposed about the third gear 66 and fourth gear 68. The gear spacer 70 is made of a metal material such as steel. The surface durability roll tester 10 includes a gear cover 72 disposed adjacent the gear spacer 70. The gear cover 72 is secured by suitable means such as screws (not shown) extending through the gear spacer 70 and top cover 58. The gear cover 72 is a generally planar and circular member having an aperture 74 extending axially therethrough. The sun driveshaft 62 extends through the aperture 74. The gear cover 72 is made of a metal material such as steel.

The surface durability roll tester 10 also includes a hydraulic cylinder 76 disposed about an end of the sun driveshaft 62 and adjacent the gear cover 72. The hydraulic cylinder 76 extends axially and has a generally circular cross-sectional shape. The hydraulic cylinder 76 is made of a metal material such as steel. The surface durability roll tester 10 also includes a cylinder piston 78 disposed within the hydraulic cylinder 76. The cylinder piston 78 extends axially and has a generally circular cross-sectional shape. The cylinder piston 76 is made of a metal material such as steel. The surface durability roll tester 10 further includes a plurality of, preferably two, seals 80 disposed within the hydraulic cylinder 76. The seals 80 are circular and planar in shape. The seals 80 are made of a flexible material such as an elastomeric material. The surface durability roll tester 10 includes a cylinder end plate 82 closing the end of the hydraulic cylinder 76. The cylinder end plate 82 is generally circular in shape and made of a metal material such as steel. The cylinder end plate 82 is secured by suitable means such as screws (not shown) to the hydraulic cylinder 76. It should be appreciated that the hydraulic cylinder 76 is connected to a source of fluid to apply fluid pressure to move the cylinder piston 78 to apply an axial force F (FIG. 3) to the sun cone 60.

Referring to FIG. 3, two pinion cones 46 and one sun cone 60 are illustrated. The geometry of the cones 46 and 60 can be made to simulate the geometry and kinematics of meshing parallel axis involute gears. The radii of the cones 46 and 60 can be made to duplicate the radii of curvature of a gear and its mating gear. The difference in the radii from one end of the cone 46,60 to the other end duplicates the changing radii of curvature found on a parallel axis involute gear. Two cones 46 and 60 contacting each other are constructed such that the amount of taper is the same on one cone 46,60 as it is on the other cone 46,60. Also, the small radii end of one cone 46,60 is in contact with the large radii end of the other cone 46,60. Contact in this manner allows the axis of each cone 46,60 to remain parallel with each other. The effect of an increasing radius on one cone 46,60 contacting a decreasing radius on the other cone 46,60 is that the effective radius of curvature can be made to duplicate a specific gear set design. It should be appreciated that the cones 46,60 are also referred to as tapered rollers.

Figures 4, 5, 6:
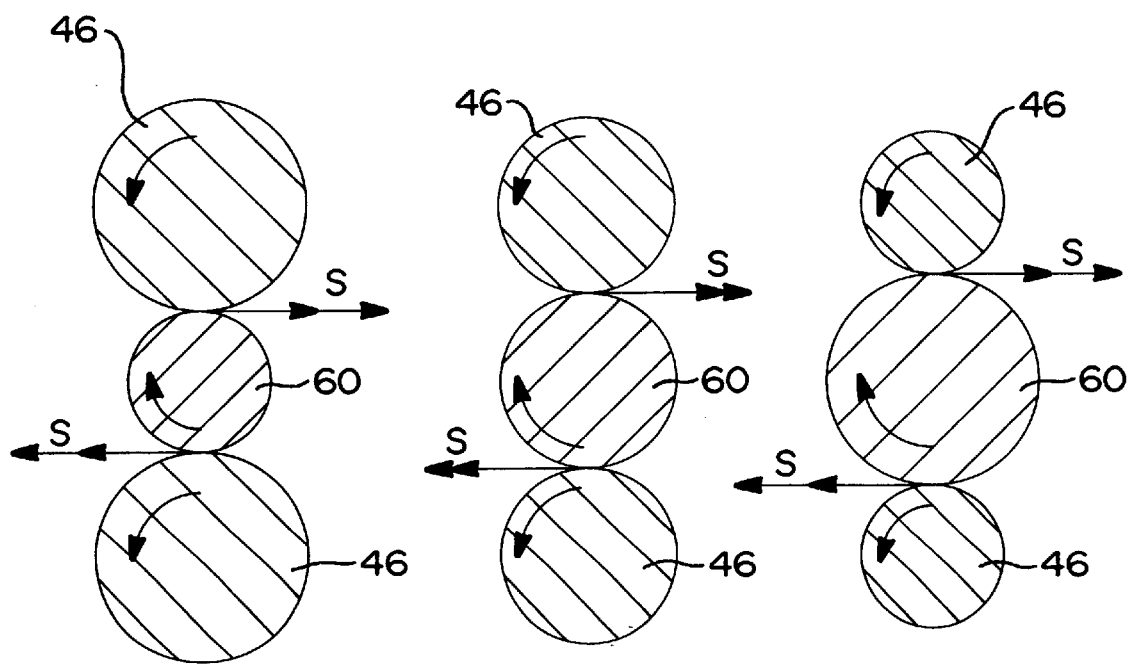
FIG. 4 is a sectional view taken along line 4—4 of FIG. 3.
FIG. 5 is a sectional view taken along line 5—5 of FIG. 3.
FIG. 6 is a sectional view taken along line 6—6 of FIG. 3.

Referring to FIGS. 3 through 6, the sun cone 60 is the tapered center roller and the pinion cones 46 are the tapered pinion rollers. As illustrated, the center roller is driven clockwise and the pinion rollers are driven counterclockwise. Driving the tapered center and pinion rollers in the same speed ratio as the gear mesh they are simulating produces a variable amount of sliding axially along the rollers. As illustrated in FIG. 4, one end of the rollers will exhibit positive sliding S, where the direction of rolling velocity and sliding velocity are in the same direction. As illustrated in FIG. 6, the other end of the rollers will exhibit negative sliding S, where the direction of sliding S is opposite direction to the rolling velocity. As illustrated in FIG. 5, at some location between the ends of the rollers there will be no sliding, the rolling velocity of both rollers will be equal. This is a feature that is also found on parallel axis involute gears. Using more than two of these tapered rollers together make it possible to apply the contact pressures to the rollers more effectively. This is done by applying an axial force F to the tapered center roller, thereby by using the geometry of the taper as a wedge to multiply the axial force to create a large normal contact pressure. Another benefit of using more than two tapered rollers is that more than one stress cycle per revolution is applied. This assures that the tapered center roller is damaged at a higher rate than the other opposing tapered pinion rollers.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A surface durability roll tester comprising:

a rotatable tapered center roller; and a plurality of rotatable tapered pinion rollers engaging said tapered centered roller to simulate gear teeth geometry and kinematics when said tapered center roller and said tapered pinion rollers are rotated.

2. A surface durability roll tester as set forth in claim 1 wherein said tapered center roller comprises a sun cone.

3. A surface durability roll tester as set forth in claim 2 wherein said sun cone has a frusta-conical shape.

4. A surface durability roll tester as set forth in claim 1 including a hydraulic cylinder operatively connected to said tapered center roller to apply an axial force to said tapered center roller.

5. A surface durability roll tester as set forth in claim 1 wherein each of said tapered pinion rollers comprises a pinion cone.

6. A surface durability roll tester as set forth in claim 5 wherein said pinion cone has a frusta-conical shape.

7. A surface durability roll tester as set forth in claim 1 including means to rotate said tapered center roller.

8. A surface durability roll tester as set forth in claim 7 including a means to rotate said tapered pinion rollers in a direction opposite to said tapered center roller.

9. A surface durability roll tester as set forth in claim 8 wherein a center of said tapered center roller and said tapered pinion rollers simulates pure rolling motion only.

10. A surface durability roll tester as set forth in claim 8 wherein a relatively large end of said tapered pinion rollers and a relatively small end of said tapered center roller simulates positive sliding motion.

11. A surface durability roll tester as set forth in claim 8 wherein a relatively large end of said tapered center roller and a relatively small end of said tapered pinion rollers simulates negative sliding motion.

12. A surface durability roll tester comprising:

a rotatable tapered center roller, said tapered center roller comprising a sun cone and a sun driveshaft connected to said sun cone;

a plurality of rotatable tapered pinion rollers engaging said tapered centered roller, each of said tapered pinion rollers comprising a pinion cone engaging said sun cone and a pinion driveshaft connected to said pinion cone; and a hydraulic cylinder operatively connected to said sun driveshaft to apply an axial force to said sun cone, whereby the tapered center roller and the tapered pinion rollers simulate gear teeth geometry and kinematics when the tapered center roller and the tapered pinion rollers are rotated.

13. A surface durability roll tester as set forth in claim 12 wherein said sun cone has a frusta-conical shape.

14. A surface durability roll tester as set forth in claim 12 wherein each of said pinion cones has a frusta-conical shape.

15. A surface durability roll tester as set forth in claim 12 including means to rotate said sun driveshaft.

16. A surface durability roll tester as set forth in claim 15 including means to rotate said pinion driveshaft in a direction opposite to said sun driveshaft.

17. A surface durability roll tester as set forth in claim 12 wherein a center of said sun cone and said pinion cones simulates pure rolling motion only.

18. A surface durability roll tester as set forth in claim 12 wherein a relatively large end of said pinion cones and a relatively small end of said sun cone simulates positive sliding motion.

19. A surface durability roll tester as set forth in claim 12 wherein a relatively large end of said sun cone and a relatively small end of said pinion cones simulates negative sliding motion.

20. A surface durability roll tester comprising:

a rotatable tapered center roller; and a plurality of rotatable tapered pinion rollers engaging said tapered centered roller, wherein a center of said tapered center roller and said tapered pinion rollers simulates pure rolling motion only, wherein a relatively large end of said tapered pinion rollers and a relatively small end of said tapered center roller simulates positive sliding motion, and wherein a relatively large end of said tapered center roller and a relatively small end of said tapered pinion rollers simulates negative sliding motion when said tapered center roller and said tapered pinion rollers are rotated.

\* \* \* \* \*